United States Patent
Fang et al.

(10) Patent No.: US 11,636,936 B2
(45) Date of Patent: Apr. 25, 2023

(54) METHOD AND APPARATUS FOR VERIFYING MEDICAL FACT

(71) Applicant: BEIJING BAIDU NETCOM SCIENCE AND TECHNOLOGY CO., LTD., Beijing (CN)

(72) Inventors: Zhou Fang, Beijing (CN); Shuangjie Li, Beijing (CN); Yabing Shi, Beijing (CN); Ye Jiang, Beijing (CN)

(73) Assignee: BEIJING BAIDU NETCOM SCIENCE AND TECHNOLOGY CO., LTD., Beijing (CN)

( * ) Notice: Subject to any disclaimer, the term of this patent is extended or adjusted under 35 U.S.C. 154(b) by 235 days.

(21) Appl. No.: 17/023,998

(22) Filed: Sep. 17, 2020

(65) Prior Publication Data

US 2021/0217504 A1 Jul. 15, 2021

(30) Foreign Application Priority Data

Jan. 14, 2020 (CN) .......................... 202010036477.0

(51) Int. Cl.
*G16H 20/10* (2018.01)
*G16H 40/67* (2018.01)
(Continued)

(52) U.S. Cl.
CPC ............ *G16H 20/10* (2018.01); *G06F 40/58* (2020.01); *G06N 20/00* (2019.01); *G16H 40/63* (2018.01); *G16H 40/67* (2018.01)

(58) Field of Classification Search
CPC .... G06F 16/258; G06F 16/3344; G06F 40/20; G06F 40/30; G06F 40/53; G06F 40/58;
(Continued)

(56) References Cited

U.S. PATENT DOCUMENTS 6,304,848 B1 * 10/2001 Singer .................... G06Q 10/10
704/215
7,295,988 B1 * 11/2007 Reeves ................... G16H 70/20
705/3

(Continued)

FOREIGN PATENT DOCUMENTS

| CN | 105894088 A | 8/2016 |
|---|---|---|
| CN | 106777966 A | 5/2017 |

(Continued)

OTHER PUBLICATIONS

Machine Learning/Deep Learning Key Concepts, published by worb1605 on Jul. 30, 2018, retrieved from https://m.blog.naver.com/PostView.naver?isHttpsRedirect=true&blogId=worb1605&logNo-221329344825, accessed Jul. 27, 2022, 32 pages.

(Continued)

*Primary Examiner* — Gerald Gauthier
(74) *Attorney, Agent, or Firm* — Knobbe, Martens, Olson & Bear, LLP (57) ABSTRACT

The present disclosure relates to the field of medical data processing based on natural language processing. Embodiments of the present disclosure disclose a method and apparatus for verifying a medical fact. The method may include: acquiring a description text of the medical fact; selecting a relevant paragraph related to the description text of the medical fact from a medical document; and inputting the description text of the medical fact and the corresponding relevant paragraph into a trained discrimination model for authenticity judgment, to obtain a verification result of the medical fact, the discrimination model being pre-trained based on a medical text paragraph pair extracted from the medical document, and being iteratively adjusted using a medical fact sample set including authenticity labeling information after the pre-training.

12 Claims, 5 Drawing Sheets

(51) Int. Cl.
*G16H 40/63* (2018.01)
*G06N 20/00* (2019.01)
*G06F 40/58* (2020.01)

(58) Field of Classification Search
CPC .............. G06F 21/6245; G06K 9/6219; G06K 9/6223; G06N 3/0445; G06N 3/0454; G06N 3/08; G06N 5/022; G06N 20/10; G06Q 10/06; G06Q 10/10; G10L 15/16; G10L 15/26; G10L 15/1815; G16H 10/60; G16H 15/00; G16H 20/00; G16H 40/63; G16H 40/67; G16H 50/20; G16H 50/30; G16H 50/70; G16H 70/20; G16H 70/60; G16Z 99/00
See application file for complete search history.

(56) References Cited

U.S. PATENT DOCUMENTS

| | | | |
|---|---|---|---|
| 8,756,079 B2* | 6/2014 | Yegnanarayanan | G10L 15/26 705/2 |
| 9,904,768 B2* | 2/2018 | Yegnanarayanan | G16Z 99/00 |
| 10,127,223 B2* | 11/2018 | Boone | G06F 40/30 |
| 11,024,406 B2* | 6/2021 | Sadeghi | G06Q 10/10 |
| 2004/0193870 A1* | 9/2004 | Redlich | G06F 21/6245 713/154 |
| 2008/0059391 A1* | 3/2008 | Rosales | G16H 50/20 703/2 |
| 2013/0085781 A1* | 4/2013 | Navani | G06Q 10/06 705/3 |
| 2017/0199963 A1* | 7/2017 | Kondadadi | G16H 15/00 |
| 2017/0300635 A1* | 10/2017 | Ganesan | G16H 15/00 |
| 2018/0121539 A1* | 5/2018 | Ciulla | G06F 16/3344 |
| 2018/0150605 A1* | 5/2018 | Co | G10L 15/16 |
| 2018/0373844 A1* | 12/2018 | Ferrandez-Escamez | G16H 50/20 |
| 2019/0006027 A1* | 1/2019 | Sacaleanu | G16H 50/30 |
| 2019/0095432 A1* | 3/2019 | Xia | G06F 40/53 |
| 2019/0130073 A1* | 5/2019 | Sun | G06K 9/6223 |
| 2019/0130282 A1* | 5/2019 | Quirk | G06N 5/022 |
| 2019/0188848 A1* | 6/2019 | Madani | G06N 3/0445 |
| 2019/0347269 A1* | 11/2019 | Xu | G06F 16/258 |
| 2020/0125639 A1* | 4/2020 | Doyle | G06F 40/30 |
| 2020/0125928 A1* | 4/2020 | Doyle | G06N 3/0445 |
| 2020/0126533 A1* | 4/2020 | Doyle | G10L 15/1815 |
| 2020/0356825 A1* | 11/2020 | Zhu | G06K 9/6219 |
| 2020/0410050 A1* | 12/2020 | Cason | G16H 50/20 |
| 2021/0217504 A1* | 7/2021 | Fang | G06F 40/20 |

FOREIGN PATENT DOCUMENTS

| | | |
|---|---|---|
| CN | 107729319 A | 2/2018 |
| CN | 109192299 A | 1/2019 |
| CN | 110297908 A | 10/2019 |
| CN | 110427486 A | 11/2019 |
| JP | 2019049964 | 3/2019 |
| KR | 10-2015-0113113 A | 10/2015 |

OTHER PUBLICATIONS

Office Action issued in JP2021-003206 dated Mar. 24, 2022.
Roth, et al., A framework for entailed relation recognition, ACL-IJCNLP 2009 Conference Short Papers, pp. 57-60 (2009).
Thorne, et al., FEVER: a large-scale dataset for Fact Extraction and VERification, arXiv:1803.05355v3 [cs.CL](2018).
Xu, et al., Using multiple features and statistical model to calculate text units similarity. IEEE, Proceedings of the Fourth International Conference on Machine Learning and Cybernetics, Guangzhou (2005).
Parkish, Ankur P., et al., "A Decomposable Attention Model for Natural Language Inference", 5 pages, arXiv:1 606.01933v1 [cs.CL] Jun. 6, 2016.

* cited by examiner

METHOD AND APPARATUS FOR VERIFYING MEDICAL FACT

CROSS-REFERENCE TO RELATED APPLICATIONS

This application claims priority to Chinese Application No. 202010036477.0, filed on Jan. 14, 2020 and entitled "Method and Apparatus for Verifying Medical Fact," the entire disclosure of which is hereby incorporated by reference.

TECHNICAL FIELD

Embodiments of the present disclosure relate to the technical field of data processing technology, specifically to the technical field of medical data processing based on natural language processing, and more specifically to a method and apparatus for verifying a medical fact.

BACKGROUND

Medical fact verification is a technology to verify the authenticity or reliability of a given medical fact. For example, if a medical fact is <kidney stone, symptom, ascites>, the verification technology may use a large amount of medical knowledge to determine the confidence degree in the medical fact and provide supporting evidence. The medical fact verification technology may be used to assist the construction of a medical knowledge graph.

With the in-depth research of artificial intelligence and deep learning technology, technologies related to natural language processing develop by leaps and bounds. Information extraction methods based on the natural language processing technology generally need to be trained on large-scale labeled data. In the field of medical fact verification, labeling of large-scale sample data has high requirements on professional knowledge and the labeling cost is high. Therefore, it is difficult to obtain a large number of labeled samples, thus it is difficult to apply a deep learning model to improve the effect of medical information extraction.

SUMMARY

Embodiments of the present disclosure propose a method and apparatus for verifying a medical fact, an electronic device and a computer readable medium.

In a first aspect, an embodiment of the present disclosure provides a method for verifying a medical fact, the method including: acquiring a description text of the medical fact; selecting a relevant paragraph related to the description text of the medical fact from a medical document; and inputting the description text of the medical fact and the corresponding relevant paragraph into a trained discrimination model for authenticity judgment, to obtain a verification result of the medical fact, the discrimination model being pre-trained based on a medical text paragraph pair extracted from the medical document, and being iteratively adjusted using a medical fact sample set including authenticity labeling information after the pre-training.

In some embodiments, the inputting the description text of the medical fact and the corresponding relevant paragraph into a trained discrimination model for authenticity judgment, to obtain a verification result of the medical fact, includes: selecting a target relevant paragraph having a highest relevance with the description text of the medical fact from the relevant paragraph using the trained discrimination model, and determining that the medical fact is a correct description in response to determining that the relevance between the target relevant paragraph and the description text of the medical fact reaches a preset threshold.

In some embodiments, the inputting the description text of the medical fact and the corresponding relevant paragraph into a trained discrimination model for authenticity judgment, to obtain a verification result of the medical fact, further includes: determining that the medical fact is a wrong description, in response to determining that the relevance between the relevant paragraph and the description text of the medical fact determined using the trained discrimination model does not reach the preset threshold.

In some embodiments, the trained discrimination model is obtained by training as follows: extracting two adjacent paragraphs from a same medical document as positive samples of the medical text paragraph pair, and extracting one paragraph from two different medical documents respectively as negative samples of the medical text paragraph pair; pre-training a constructed initial discrimination model based on the positive samples and the negative samples of the medical text paragraph pairs; acquiring the medical fact sample set including authenticity labeling information, wherein the authenticity labeling information includes labeling information for labeling whether a medical fact sample is a correct description; and adjusting iteratively the pre-trained discrimination model based on the medical fact sample set to obtain the trained discrimination model.

In some embodiments, the authenticity labeling information further includes a medical document paragraph that serves as supporting evidence for the medical fact sample when the medical fact sample is the correct description; and the verification result of the medical fact includes a verification result of whether the medical fact is the correct description and a medical document paragraph that serves as supporting evidence for the medical fact when the medical fact is the correct description.

In a second aspect, an embodiment of the present disclosure provides an apparatus for verifying a medical fact, the apparatus including: an acquisition unit, configured to acquire a description text of the medical fact; a selection unit, configured to select a relevant paragraph related to the description text of the medical fact from a medical document; and a discrimination unit, configured to input the description text of the medical fact and the corresponding relevant paragraph into a trained discrimination model for authenticity judgment, to obtain a verification result of the medical fact, the discrimination model being pre-trained based on a medical text paragraph pair extracted from the medical document, and being iteratively adjusted using a medical fact sample set including authenticity labeling information after the pre-training.

In some embodiments, the discrimination unit is configured to verify the medical fact as follows: selecting a target relevant paragraph having a highest relevance with the description text of the medical fact from the relevant paragraph using the trained discrimination model, and determining that the medical fact is a correct description in response to determining that the relevance between the target relevant paragraph and the description text of the medical fact reaches a preset threshold.

In some embodiments, the discrimination unit is further configured to verify the medical fact as follows: determining that the medical fact is a wrong description, in response to determining that the relevance between the relevant paragraph and the description text of the medical fact determined using the trained discrimination model does not reach the preset threshold.

In some embodiments, the apparatus further includes a training unit, configured to generate the trained discrimination model as follows: extracting two adjacent paragraphs from a same medical document as positive samples of the medical text paragraph pair, and extracting one paragraph from two different medical documents respectively as negative samples of the medical text paragraph pair; pre-training a constructed initial discrimination model based on the positive samples and the negative samples of the medical text paragraph pairs; acquiring the medical fact sample set including authenticity labeling information, wherein the authenticity labeling information includes labeling information for labeling whether a medical fact sample is a correct description; and adjusting iteratively the pre-trained discrimination model based on the medical fact sample set to obtain the trained discrimination model.

In some embodiments, the authenticity labeling information further includes a medical document paragraph that serves as supporting evidence for the medical fact sample when the medical fact sample is the correct description; and the verification result of the medical fact includes a verification result of whether the medical fact is the correct description and a medical document paragraph that serves as supporting evidence for the medical fact when the medical fact is the correct description.

In a third aspect, an embodiment of the present disclosure provides an electronic device, the device electronic including: one or more processors; and a storage apparatus, for storing one or more programs, where the one or more programs, when executed by the one or more processors, cause the one or more processors to implement the method for verifying a medical fact according to the first aspect.

In a fourth aspect, an embodiment of the present disclosure provides a computer readable medium, storing a computer program thereon, where the computer program, when executed by a processor, implements the method for verifying a medical fact according to the first aspect.

According to the method and apparatus for verifying a medical fact of embodiments of the present disclosure, by acquiring a description text of the medical fact; selecting a relevant paragraph related to the description text of the medical fact from a medical document; and inputting the description text of the medical fact and the corresponding relevant paragraph into a trained discrimination model for authenticity judgment, to obtain a verification result of the medical fact, the discrimination model being pre-trained based on a medical text paragraph pair extracted from the medical document, and being iteratively adjusted using a medical fact sample set including authenticity labeling information after the pre-training, the accurate verification of medical facts using a medical fact discrimination model obtained by trained based on a small number of labeled samples is realized, the cost of sample labeling for medical fact verification using a deep learning method is reduced, thereby reducing the cost of verifying a medical fact. Moreover, the discrimination model in the present solution may learn from a wide range of medical documents, so that it may be applied to the verification of a large number of extensive medical facts, and may help improve the efficiency and accuracy of medical information extraction.

BRIEF DESCRIPTION OF THE DRAWINGS

After reading detailed descriptions of non-limiting embodiments with reference to the following accompanying drawings, other features, objectives and advantages of the present disclosure will become more apparent.

DETAILED DESCRIPTION OF EMBODIMENTS

Embodiments of present disclosure will be described below in detail with reference to the accompanying drawings. It should be appreciated that the specific embodiments described herein are merely used for explaining the relevant disclosure, rather than limiting the disclosure. In addition, it should be noted that, for the ease of description, only the parts related to the relevant disclosure are shown in the accompanying drawings.

It should also be noted that some embodiments in the present disclosure and some features in the disclosure may be combined with each other on a non-conflict basis. Features of the present disclosure will be described below in detail with reference to the accompanying drawings and in combination with embodiments.

Figure 1:
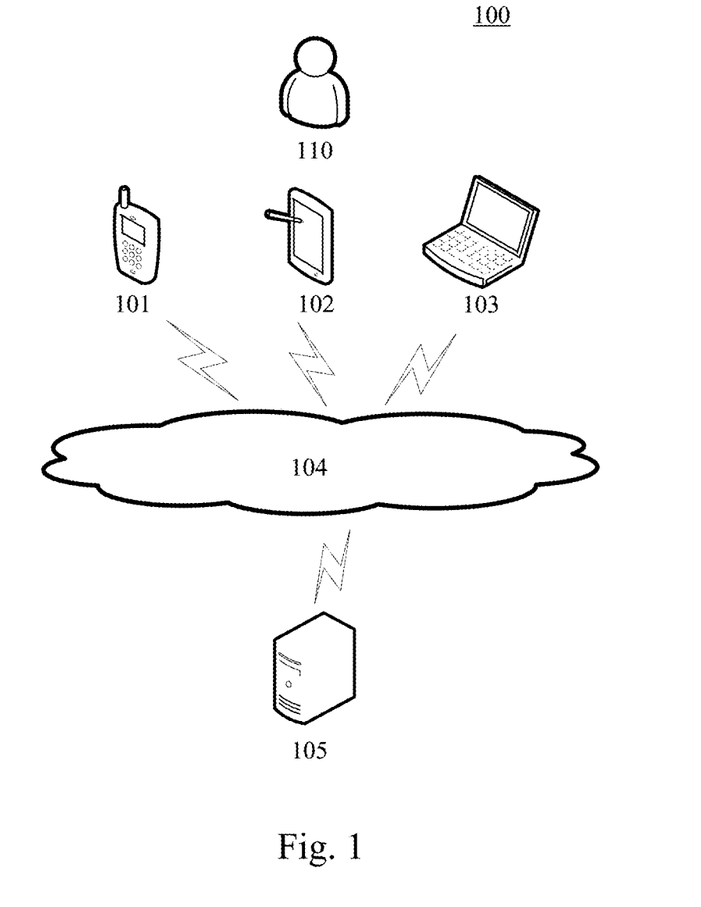
FIG. 1 is a diagram of an example system architecture in which embodiments of the present disclosure may be implemented.

FIG. 1 illustrates an example system architecture 100 in which a method for verifying a medical fact or an apparatus for verifying a medical fact according to the present disclosure may be implemented.

As shown in FIG. 1, the system architecture 100 may include terminal devices 101, 102, 103, a network 104 and a server 105. The network 104 serves as a medium providing a communication link between the terminal devices 101, 102, 103 and the server 105. The network 104 may include various types of connections, such as wired or wireless communication links, or optic fibers.

The terminal devices 101, 102, and 103 interact with the server 105 through the network 104 to receive or send messages or the like. The terminal devices 101, 102, 103 may be client devices, on which various client applications may be installed.

The terminal devices 101, 102, and 103 may be hardware or software. When the terminal devices 101, 102, and 103 are hardware, the terminal devices 101, 102, and 103 may be various electronic devices, including but not limited to smart phones, tablet computers, e-book readers, laptop portable computers, desktop computers and the like. When the terminal devices 101, 102, and 103 are software, the terminal devices 101, 102, and 103 may be installed in the electronic devices listed above. The terminal devices 101, 102, and 103 may be implemented as a plurality of software programs or software modules (for example, a plurality of software programs or software modules for providing distributed services), or as a single software program or software module. The present disclosure is not specifically limited herein.

The server 105 may be a server running various services, for example, a server running a medical knowledge base maintenance service, or a server running a medical auxiliary diagnosis service. The server 105 may acquire uploaded medical-related data from the terminal devices 101, 102, 103, such as medical records, diagnosis and medication reports, description information of medical facts, medical knowledge data, medical query data, labeling data of medical fact samples, or the like. The server 105 may also receive medical fact verification requests from the terminal devices 101, 102, 103, etc., parse the medical fact verification requests, verify medical facts therein, and feed back verification results to the terminal devices 101, 102, 103. The server 105 may also construct a medical graph based on the verification results of the medical facts. For example, after determining that a medical fact is a correct description, medical knowledge described in the medical fact may be added to the medical graph.

It should be noted that the method for verifying a medical fact provided by embodiments of the present disclosure is generally performed by the server 105. Accordingly, the apparatus for verifying a medical fact is generally provided in the server 105.

In some scenarios, the server 105 may acquire to-be-processed medical fact data from a database, a memory, or other servers. In this regard, the example system architecture 100 may not include the terminal devices 101, 102, 103 and/or the network 104.

It should be noted that the server 105 may be hardware or software. When the server 105 is hardware, the server 105 may be implemented as a distributed server cluster composed of a plurality of servers, or as a single server. When the server 105 is software, the server 105 may be implemented as a plurality of software programs or software modules (for example, a plurality of software programs or software modules for providing distributed services), or as a single software program or software module. The present disclosure is not specifically limited herein.

It should be understood that the numbers of terminal devices, networks and servers in FIG. 1 are merely illustrative. Depending on the implementation needs, there may be any number of terminal devices, networks and servers.

Figure 2:
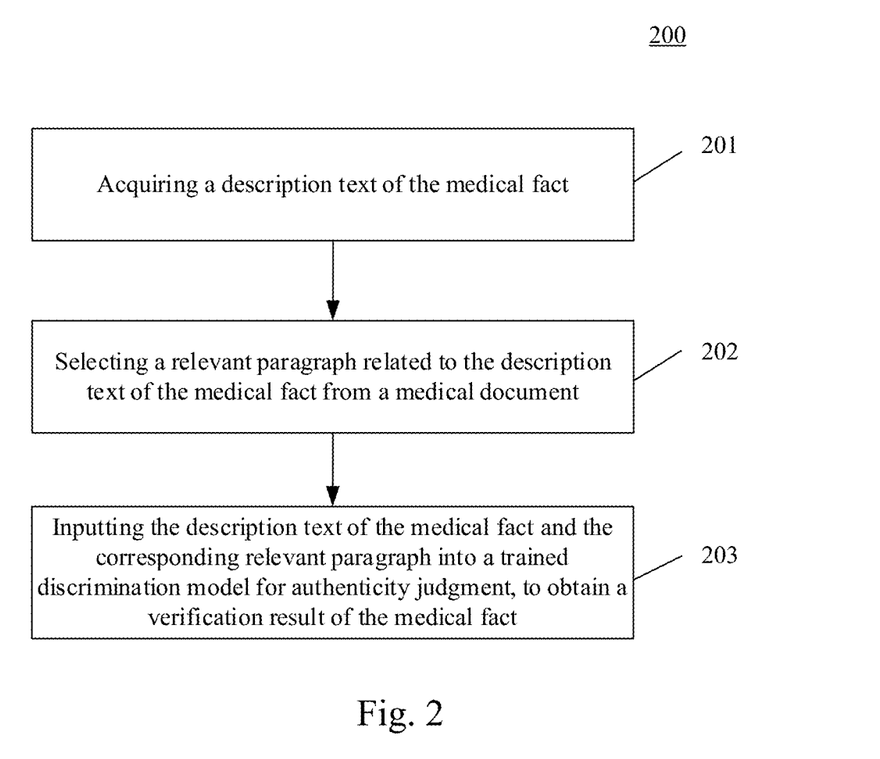
FIG. 2 is a flowchart of a method for verifying a medical fact according to an embodiment of the present disclosure.

With further reference to FIG. 2, a flow 200 of a method for verifying a medical fact according to an embodiment of the present disclosure is illustrated. The flow 200 of the method for verifying a medical fact includes the following steps.

Step 201, acquiring a description text of the medical fact.

In the present embodiment, an executing body of the method for verifying a medical fact (the server as shown in FIG. 1) may acquire the description text of the medical fact to be judged. Here, the medical fact may be a description of a corresponding relationship between any two or more of topics of medical activities such as diseases, symptoms, transmission routes, treatment methods, administration methods, or applicable populations. The description text of the medical fact may include text describing the above corresponding relationship.

In the present embodiment, the medical fact may be described in the form of <s, p, o>, where s and o represent any two of the above topics in the medical activities, and p represents the relationship between s and o. As an example, a medical fact is <kidney stone, symptom, ascites>, in which "kidney stone" represents a disease, and "ascites" is a "symptom" of "kidney stone". As another example, a medical fact is <measles, transmission route, droplets>, in which "measles" is a disease, and "droplets" is a "transmission route" of "measles".

In the present embodiment, the description text of the medical fact may be manually created. In medical research or practice, if it is found that there may be a certain relationship between two topics of the medical activities, a corresponding medical fact may be created, and medical fact verification technology may be used to verify whether the created medical fact is a correct description.

Step 202, selecting a relevant paragraph related to the description text of the medical fact from a medical document.

In the present embodiment, a pre-constructed medical document set may be acquired. In practice, reliable medical documents such as relevant literature, books, medical records, or treatment manuals in the medical field may be collected to construct the medical document set.

Then, the medical documents in the medical document set may be preprocessed, the contents of the documents may be read, and the documents may be divided into paragraph granularities based on the font in the document, the format of image content, and specific position identifier (such as line break), etc. to obtain a plurality of medical document paragraphs.

After that, a relevance analysis may be performed on the medical document paragraphs and the description text of the medical fact obtained in step 201, to select the relevant paragraph related to the description text of the medical fact.

Specifically, word segmentation may be performed on the description text of the medical fact, to extract a medical keyword, for example, extract a medical keyword that describes a feature such as a symptom, a disease, a drug, an administration method, or a transmission method. Then, it may be judged whether the medical document paragraph hits the extracted medical keyword. If the medical document paragraph hits the extracted medical keyword, it may be determined that the medical document paragraph is the relevant paragraph related to the description text of the medical fact; otherwise, it may be determined that the medical document paragraph is not a relevant paragraph related to the description text of the medical fact.

When judging whether a medical document paragraph hits the medical keyword extracted from the description text of the medical fact, a hit judgment method based on exact matching or semantic similarity matching may be used. The exact matching method is to judge whether the medical document paragraph includes the medical keyword extracted from the description text of the medical fact. The method based on semantic similarity matching may be specifically performed as follows: first, splitting the medical text paragraph into a word sequence, converting the word sequence and the medical keyword in the description text of the medical fact into corresponding feature vectors, and then calculating a semantic similarity between each word in the word sequence and the medical keyword in the description text of the medical fact. If the semantic similarity of the two exceeds a preset semantic similarity threshold, it is determined that the medical text paragraph hits the medical keyword in the description text of the medical fact.

Step 203, inputting the description text of the medical fact and the corresponding relevant paragraph into a trained discrimination model for authenticity judgment, to obtain a verification result of the medical fact.

The description text of the medical fact and the relevant paragraph related to the description text of the medical fact determined in step 202 may be inputted into the trained discrimination model. The trained discrimination model may be constructed based on a neural network structure such as a convolutional neural network or a cyclic neural network, and the trained discrimination model may determine whether the description text of the medical fact is consistent with the description of each relevant paragraph. If a discrimination result of the discrimination model is that the relevant paragraphs determined in step 202 does not include a paragraph that is consistent in semantics with the description text of the medical fact, it may be determined that the description of the medical fact is wrong; and if the discrimination result of the discrimination model is that a relevant paragraph is consistent in semantics with the description text of the medical fact, it may be determined that the description of the medical fact is correct.

The above discrimination model is obtained by training as follows: pre-training based on a medical text paragraph pair extracted from the medical document, and adjusting iteratively using a medical fact sample set including authenticity labeling information after the pre-training.

Specifically, in the pre-training, medical text paragraph pairs may be extracted from the medical document, and each medical text paragraph pair includes two related or unrelated medical text paragraphs. Parameters of the discrimination model may be adjusted based on a deviation of a discrimination result of the discrimination model on whether the two medical paragraphs in the medical text paragraph pair are related.

After the pre-training is completed, a small-scale medical fact sample set may be used to perform supervised training on the discrimination model to further optimize the parameters of the discrimination model. The medical fact sample set includes medical fact samples having authenticity labeling information. The authenticity labeling information represents whether a medical fact sample is a correct description. A loss function may be constructed based on a difference between an authenticity discrimination result of the medical fact sample by the discrimination model and the authenticity labeling information of the medical fact sample, and the parameters of the discrimination model may be adjusted iteratively based on the loss function, until the loss function reaches a predetermined convergence condition, to obtain the trained discrimination model.

According to the method for verifying a medical fact of the above embodiment, by acquiring a description text of the medical fact; selecting a relevant paragraph related to the description text of the medical fact from a medical document; and inputting the description text of the medical fact and the corresponding relevant paragraph into a trained discrimination model for authenticity judgment, to obtain a verification result of the medical fact, the discrimination model being pre-trained based on a medical text paragraph pair extracted from the medical document, and being iteratively adjusted using a medical fact sample set including authenticity labeling information after the pre-training, medical fact verification based on a deep learning model is realized. The method may perform accurate verification on medical facts using a medical fact discrimination model obtained by training based on a small number of labeled samples, may reduce the cost of sample labeling for medical fact verification using a deep learning method, thereby reducing the cost of verifying a medical fact. Moreover, the discrimination model in the present solution may learn from a wide range of medical documents, so that it may be applied to the verification of a large number of extensive medical facts.

In some alternative implementations of the present embodiment, the verification result of the medical fact may be obtained as follows: selecting a target relevant paragraph having the highest relevance with the description text of the medical fact from the relevant paragraphs using the trained discrimination model, and determining that the medical fact is a correct description in response to determining that the relevance between the target relevant paragraph and the description text of the medical fact reaches a preset threshold.

Specifically, the trained discrimination model may be used to score the relevance between the description text of the medical fact and each relevant paragraph, select the relevant paragraph having the highest relevance as the target relevant paragraph after sorting by score, and further determine whether the relevance between the target relevant paragraph and the description text of the medical fact reaches the preset threshold, if the relevance between the target relevant paragraph and the description text of the medical fact reaches the preset threshold, it is determined that the medical fact is a correct description.

Further, if it is determined that the relevance between the target relevant paragraph of the description text of the medical fact and the description text of the medical fact does not reach the preset threshold, or the relevance between each relevant paragraph of the description text of the medical fact and the description text of the medical fact does not reach the preset threshold, it may be determined that the medical fact is a wrong description.

In this way, it is possible to further determine whether the description text of the medical fact is authentic and credible by determining whether the maximum value of the relevance with the description text of the medical fact in each relevant paragraph reaches the preset threshold, thereby further improving the reliability of the verification result.

Figure 3:
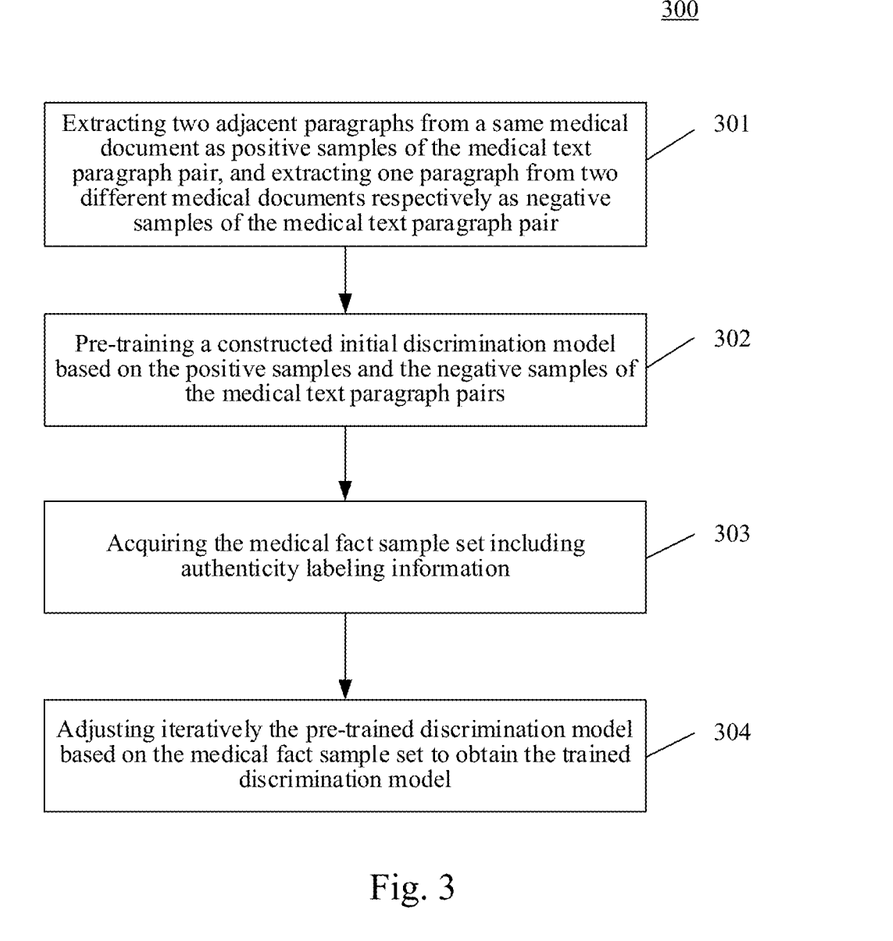
FIG. 3 is a schematic flowchart of a training method for a discrimination model.

The above discrimination model may be pre-trained and stored in the executing body of the method for verifying a medical fact, or trained by another electronic device and run in the executing body of the method for verifying a medical fact. With further reference to FIG. 3, a schematic flowchart of an implementation of a training method for the discrimination model is illustrated. As shown in FIG. 3, the discrimination model may be obtained by training according to the flow 300 as follows.

Step 301, extracting two adjacent paragraphs from a same medical document as positive samples of the medical text paragraph pair, and extracting one paragraph from two different medical documents respectively as negative samples of the medical text paragraph pair.

Paragraph pairs may be formed by extracting paragraphs from a large number of medical documents to construct medical text paragraph pairs. Two adjacent paragraphs of the same medical document are generally naturally consecutive and the medical knowledge described are consistent. Paragraphs randomly extracted from two medical documents are generally not naturally consecutive. For example, the topic of a paragraph randomly extracted from one of the medical documents is the prevention of infectious diseases, and a paragraph randomly extracted from another medical document is the treatment of kidney stones, then these two paragraphs are generally not naturally consecutive. The positive samples for pre-training the discrimination model may be constructed based on two consecutive paragraphs extracted from the same medical document, and two paragraphs randomly extracted from different medical documents may be used as the negative samples for training the discrimination model.

The positive samples and the negative samples of the medical text paragraph pairs may not include manually labeled labeling information.

Step 302, pre-training a constructed initial discrimination model based on the positive samples and the negative samples of the medical text paragraph pairs.

The initial discrimination model may be constructed based on a convolutional neural network or a cyclic neural network, etc., and parameters of the initial discrimination model may be set.

Figure 4:
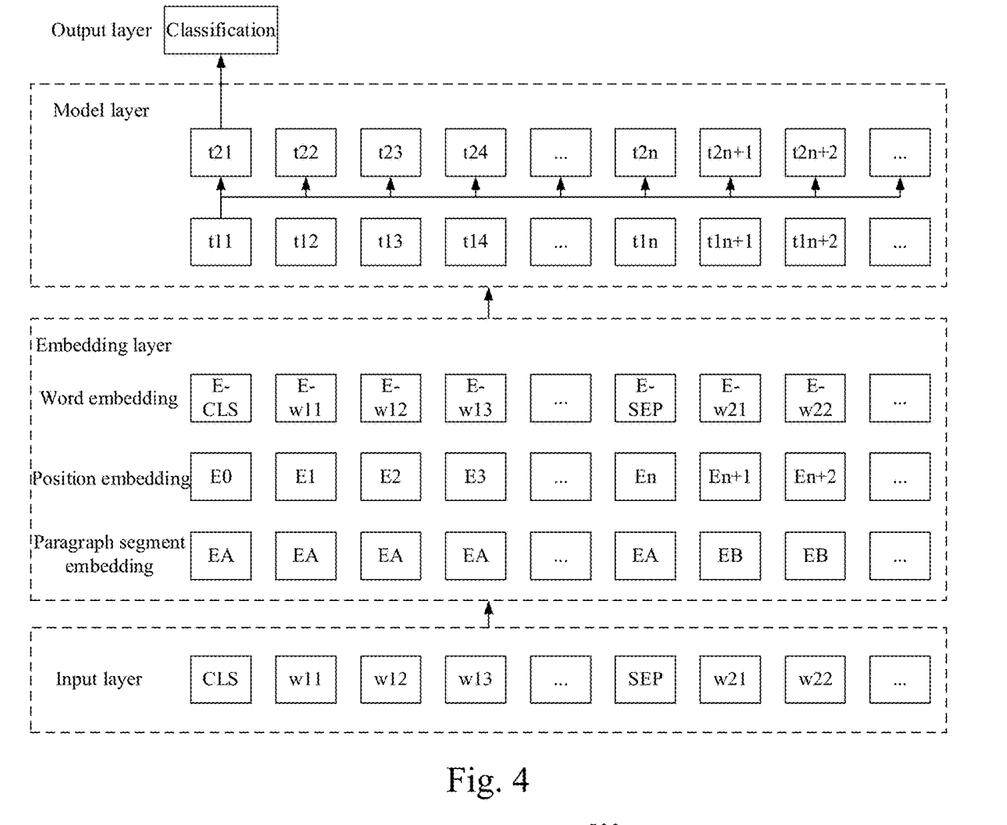
FIG. 4 is a schematic structural diagram of a discrimination model.

With reference to FIG. 4, a schematic structural diagram of the above discrimination model is illustrated. In the present embodiment, the initial discrimination model may be constructed according to a structure shown in FIG. 4. As shown in FIG. 4, the discrimination model may include an input layer, an embedding layer, a model layer, and an output layer.

The input layer represents an input of the model, and the input of the model is a sequence after word segmentation of two text paragraphs or a sequence after word segmentation of two paragraph descriptions. A tag element (such as CLS) may be added at the beginning of the sequence to identify whether the two paragraphs are adjacent in the actual text or whether the two paragraph descriptions are consistent. Another tag element (such as SEP) may be added between the two text paragraphs or between the two paragraph descriptions to identify a position of division between the two text paragraphs or between the two paragraph descriptions. In FIG. 4, w11, w12, w13, . . . represent a word sequence after the word segmentation of the first text paragraph, and w21, w22, . . . represent a word sequence after the word segmentation of the second text paragraph.

The embedding layer may include a plurality of embedding modules, and each embedding module performs feature extraction on the sequence inputted by the input layer. Methods of word embedding, position embedding and paragraph segment embedding may be used for feature extraction respectively. Here, word embedding may convert an inputted word into a corresponding word tag using a vocabulary, and compress the word tag into a corresponding word vector by embedding; position embedding converts position information of the word in the inputted sequence into a corresponding position vector using an embedding method; and paragraph segment embedding is used to convert information that represents the paragraph to which each word belongs to a corresponding paragraph segment vector using the embedding method. In FIG. 4, EA indicates that the paragraph to which the word belongs is the first text paragraph, and EB indicates that the paragraph to which the word belongs is the second text paragraph; E0, E1, E2, E3, . . . , En, En+1, En+2 represent position embedding vectors corresponding to the words in the input layer in one-to-one correspondence; and E-CLS, E-w11, E-w12, E-w13, . . . , E-w21, E-w22, . . . represent word vectors corresponding to the words in the input layer in one-to-one correspondence.

Each of the model layers may include a plurality of transformer units. The transformer unit is used to further transform and calculate features extracted by the embedding layer. The transformer unit may include an encoder and a decoder, where the encoder may include a self attention layer and a feedforward neural network, and the decoder may also include a self attention layer and a feedforward neural network. The transformer units of the model layer correspond to the elements of the input layer and the embedding modules of the embedding layer in one-to-one correspondence, transformer units on the same layer are not connected to each other, and transformer units on two adjacent layers are connected in pairs. FIG. 4 shows two layers of transformer units, the first layer of transformer units includes t11, t12, t13, t14, . . . , t1n, t1n+1, t1n+2, . . . ; and the second layer of transformer units include t21, t22, t23, t24, . . . , t2n, t2n+1, t2n+2, . . . ; which schematically shows that the transformer unit t11 of the first layer is connected to each transformer unit of the second layer respectively.

An output of the output layer is a judgment result of whether the inputted two text paragraphs or two paragraph descriptions are naturally consecutive, which may be a classification tag.

After acquiring the initial discrimination model, the positives sample and the negative samples of the medical text paragraph pairs are inputted into the discrimination model, and the discrimination model may determine whether the inputted medical text paragraph pair is of naturally consecutive two paragraphs. The pre-trained loss function is constructed based on a judgment error of the discrimination model. If the current value of the loss function does not meet a pre-trained convergence condition, the gradient descent method is used to adjust the parameters of the discrimination model, and the parameter-adjusted discrimination model is used to re-judge the medical text paragraph pair. If the loss function calculated based on the judgment error does not meet the pre-trained convergence condition, then the parameters of the discrimination model are still adjusted. In this way, by repeatedly adjusting the parameters of the discrimination model for multiple times, the judgment error of the discrimination model is gradually reduced, and when the error of the discrimination model is reduced to a certain range or the parameter adjustment operation of the discrimination model is performed to reach a certain number of times, the parameters of the discrimination model may be fixed to obtain the pre-trained discrimination model.

Step 303, acquiring the medical fact sample set including authenticity labeling information.

Here, the authenticity labeling information includes labeling information for labeling whether a medical fact sample is a correct description. The authenticity labeling information may be manual labeling information. In practice, small-scale medical fact samples may be constructed and the authenticity of the medical fact samples may be labeled.

Step 304, adjusting iteratively the pre-trained discrimination model based on the medical fact sample set to obtain the trained discrimination model.

The pre-trained discrimination model may be used to judge the authenticity of the medical fact samples in the medical fact sample set. Specifically, a relevant paragraph related to a description text of the medical fact sample may be selected from a medical document set, and then the description text of the medical fact sample and the corresponding relevant paragraph are inputted into the pre-trained discrimination model, and the pre-trained discrimination model is used to judge whether the description text of the medical fact sample and the corresponding relevant paragraph are naturally consecutive texts. The output of the discrimination model may be a probability value of the confidence degree that represents the description text of the medical fact sample and the corresponding relevant paragraph are naturally consecutive texts, or may be category tags corresponding to the two categories of "correct description" and "wrong description" to which the probability value is mapped. If the discrimination model judges that the description text of the medical fact sample and the corresponding relevant paragraph are naturally consecutive texts, the judgment result is that the medical fact sample is a correct description, otherwise the medical fact sample is a wrong description.

The judgment error of the discrimination model may be calculated based on authenticity labeling information of the medical fact sample set, and the judgment error of the discrimination model on the medical fact sample set is gradually reduced when the parameters of the pre-trained discrimination model are iteratively adjusted for multiple times. When a preset times of iterative adjustment operations are completed or the judgment error of the discrimination model on the medical fact sample set is reduced to a preset range, the adjustment of the parameters of the discrimination model is stopped to obtain the trained discrimination model.

In some embodiments, the authenticity labeling information further includes a medical document paragraph that serves as supporting evidence for the medical fact sample when the medical fact sample is the correct description. That is, when labeling, it is also possible to select a medical paragraph that matches the text description of the correct medical fact sample and has consistent semantics with the text description of the correct medical fact sample from the medical document as supporting evidence for the correct medical fact sample. In this regard, the verification result of the medical fact includes a verification result of whether the medical fact is the correct description and a medical document paragraph that serves as supporting evidence for the medical fact when the medical fact is the correct description.

In this way, in the process of training the discrimination model based on the medical fact sample set, the discrimination model may learn the inner logic of selecting from a plurality of relevant paragraphs as the supporting evidence for the correct medical fact, so that the discrimination model may provide more reliable evidence support for the verification result of the medical fact.

The method for verifying a medical fact may be applied to medical graph construction. In some embodiments, the flow of the method for verifying a medical fact may further include: updating a medical knowledge base based on the verification result that the medical fact is the correct description, and updating a medical knowledge graph based on the updated medical knowledge base. In this regard, the medical knowledge base may be efficiently and reliably expanded through high-accuracy medical fact verification.

In some embodiments, the verification result of the medical fact may also be pushed to a user, so that the user may use the verification result as auxiliary information to update the knowledge base, thereby helping to improve the efficiency of medical knowledge extraction and medical knowledge base construction.

Figure 5:
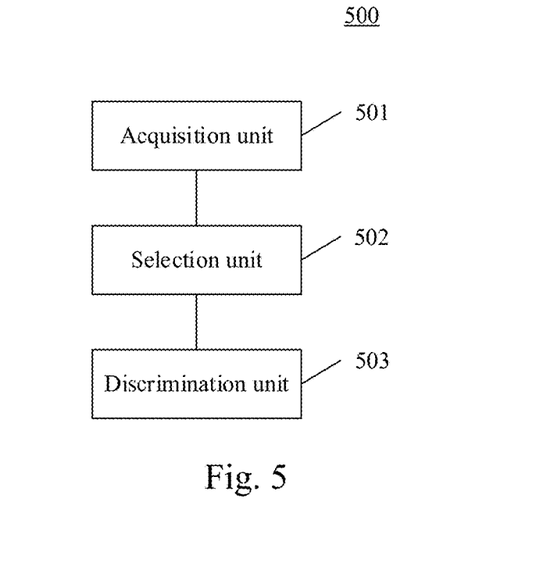
FIG. 5 is a schematic structural diagram of an apparatus for verifying a medical fact according to an embodiment of the present disclosure.

With reference to FIG. 5, as an implementation of the method for verifying a medical fact, an embodiment of the present disclosure provides an apparatus for verifying a medical fact, and the apparatus embodiment may correspond to the method embodiment as shown in FIG. 2, and the apparatus may be specifically applied to various electronic devices.

As shown in FIG. 5, an apparatus 500 for verifying a medical fact of the present embodiment includes an acquisition unit 501, a selection unit 502 and a discrimination unit 503. The acquisition unit 501 is configured to acquire a description text of the medical fact. The selection unit 502 is configured to select a relevant paragraph related to the description text of the medical fact from a medical document. The discrimination unit 503 is configured to input the description text of the medical fact and the corresponding relevant paragraph into a trained discrimination model for authenticity judgment, to obtain a verification result of the medical fact, the discrimination model being pre-trained based on a medical text paragraph pair extracted from the medical document, and being iteratively adjusted using a medical fact sample set including authenticity labeling information after the pre-training.

In some embodiments, the discrimination unit 503 is configured to verify the medical fact as follows: selecting a target relevant paragraph having the highest relevance with the description text of the medical fact from the relevant paragraph using the trained discrimination model, and determining that the medical fact is a correct description in response to determining that the relevance between the target relevant paragraph and the description text of the medical fact reaches a preset threshold.

In some embodiments, the discrimination unit 503 is further configured to verify the medical fact as follows: determining that the medical fact is a wrong description, in response to determining that the relevance between the relevant paragraph and the description text of the medical fact determined using the trained discrimination model does not reach the preset threshold.

In some embodiments, the apparatus further includes a training unit, configured to generate the trained discrimination model as follows: extracting two adjacent paragraphs from the same medical document as positive samples of the medical text paragraph pair, and extracting one paragraph from two different medical documents respectively as negative samples of the medical text paragraph pair; pre-training a constructed initial discrimination model based on the positive samples and the negative samples of the medical text paragraph pairs; acquiring the medical fact sample set including authenticity labeling information, where the authenticity labeling information includes labeling information for labeling whether a medical fact sample is a correct description; and adjusting iteratively the pre-trained discrimination model based on the medical fact sample set to obtain the trained discrimination model.

In some embodiments, the authenticity labeling information further includes a medical document paragraph that serves as supporting evidence for the medical fact sample when the medical fact sample is the correct description; and the verification result of the medical fact includes a verification result of whether the medical fact is the correct description and a medical document paragraph that serves as supporting evidence for the medical fact when the medical fact is the correct description.

The units in the apparatus 500 correspond to the steps in the method described with reference to FIG. 2. Therefore, the operations, features, and technical effects that can be achieved described with respect to the method for verifying a medical fact are also applicable to the apparatus 500 and the units contained therein, and detailed description thereof will be omitted.

Figure 6:
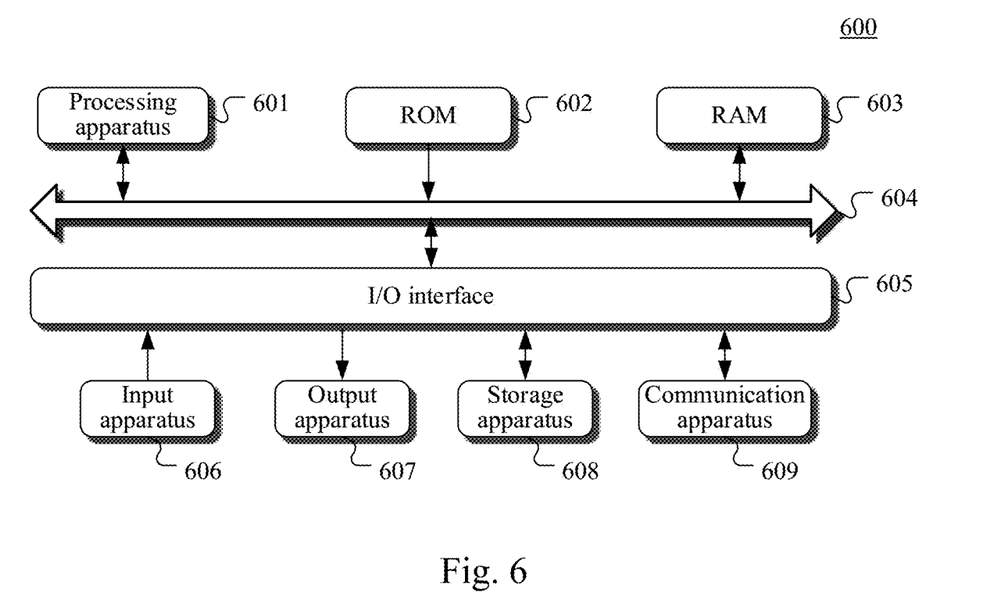
FIG. 6 is a schematic structural diagram of a computer system adapted to implement an electronic device according to embodiments of the present disclosure.

With reference to FIG. 6, a schematic structural diagram adapted to implement an electronic device (for example, the server shown in FIG. 1) 600 according to embodiments of the present disclosure is shown. The electronic device shown in FIG. 6 is merely an example, and should not impose any limitation on the function and scope of use of embodiments of the present disclosure.

As shown in FIG. 6, the electronic device 600 may include a processing apparatus (for example, a central processor, a graphics processor, etc.) 601, which may execute various appropriate actions and processes in accordance with a program stored in a read-only memory (ROM) 602 or a program loaded into a random access memory (RAM) 603 from a storage apparatus 608. The RAM 603 also stores various programs and data required by operations of the electronic device 600. The processing apparatus 601, the ROM 602 and the RAM 603 are connected to each other through a bus 604. An input/output (I/O) interface 605 is also connected to the bus 604.

Generally, the following apparatuses may be connected to the I/O interface 605: an input apparatus 606, including such as a touch screen, a touch pad, a keyboard, a mouse, a camera, a microphone, an accelerometer, or a gyroscope; an output apparatus 607 including such as a liquid crystal display (LCD), a speaker, or a vibrator; the storage apparatus 608 including such as a hard disk; and a communication apparatus 609. The communication apparatus 609 may allow the electronic device 600 to perform wireless or wired communication with other devices to exchange data. Although FIG. 6 shows the electronic device 600 having various apparatuses, it should be understood that it is not required to implement or have all the apparatuses shown. More or fewer apparatuses may be implemented or provided instead. Each block shown in FIG. 6 may represent one apparatus, and may also represent a plurality of apparatuses as required.

In particular, according to embodiments of the present disclosure, the process described above with reference to the flow chart may be implemented in a computer software program. For example, an embodiment of the present disclosure includes a computer program product, which includes a computer program that is embedded in a computer readable medium. The computer program includes program codes for performing the method as illustrated in the flow chart. In such an embodiment, the computer program may be downloaded and installed from a network through the communication apparatus 609, or installed from the storage apparatus 608, or installed from the ROM 602. The computer program, when executed by the processing apparatus 601, implements the above mentioned functionalities as defined in the method of embodiments of the present disclosure. It should be noted that the computer readable medium according to some embodiments of the present disclosure may be a computer readable signal medium or a computer readable medium or any combination of the above two. An example of the computer readable medium may include, but is not limited to: electric, magnetic, optical, electromagnetic, infrared, or semiconductor systems, apparatuses, elements, or a combination of any of the above. A more specific example of the computer readable medium may include, but is not limited to: electrical connection with one or more pieces of wire, a portable computer disk, a hard disk, a random access memory (RAM), a read only memory (ROM), an erasable programmable read only memory (EPROM or flash memory), an optical fiber, a portable compact disk read only memory (CD-ROM), an optical memory, a magnetic memory, or any suitable combination of the above. In some embodiments of the present disclosure, the computer readable medium may be any tangible medium containing or storing programs, which may be used by, or used in combination with, a command execution system, apparatus or element. In some embodiments of the present disclosure, the computer readable signal medium may include a data signal in the base band or propagating as a part of a carrier wave, in which computer readable program codes are carried. The propagating data signal may take various forms, including but not limited to an electromagnetic signal, an optical signal, or any suitable combination of the above. The computer readable signal medium may also be any computer readable medium except for the computer readable medium. The computer readable medium is capable of transmitting, propagating or transferring programs for use by, or used in combination with, a command execution system, apparatus or element. The program codes contained on the computer readable medium may be transmitted with any suitable medium, including but not limited to: wireless, wired, optical cable, RF medium, etc., or any suitable combination of the above.

The computer readable medium may be included in the above electronic device, or a stand-alone computer readable medium not assembled into the electronic device. The computer readable medium carries one or more programs. The one or more programs, when executed by the electronic device, cause the electronic device to: acquire a description text of the medical fact; select a relevant paragraph related to the description text of the medical fact from a medical document; and input the description text of the medical fact and the corresponding relevant paragraph into a trained discrimination model for authenticity judgment, to obtain a verification result of the medical fact, the discrimination model being pre-trained based on a medical text paragraph pair extracted from the medical document, and being iteratively adjusted using a medical fact sample set including authenticity labeling information after the pre-training.

A computer program code for executing operations in some embodiments of the present disclosure may be compiled using one or more programming languages or combinations thereof. The programming languages include object-oriented programming languages, such as Java, Smalltalk or C++, and also include conventional procedural programming languages, such as "C" language or similar programming languages. The program code may be completely executed on a user's computer, partially executed on a user's computer, executed as a separate software package, partially executed on a user's computer and partially executed on a remote computer, or completely executed on a remote computer or server. In a circumstance involving a remote computer, the remote computer may be connected to a user's computer through any network, including local area network (LAN) or wide area network (WAN), or be connected to an external computer (for example, connected through the Internet using an Internet service provider).

The flow charts and block diagrams in the accompanying drawings illustrate architectures, functions and operations that may be implemented according to the systems, methods and computer program products of the various embodiments of the present disclosure. In this regard, each of the blocks in the flow charts or block diagrams may represent a module, a program segment, or a code portion, said module, program segment, or code portion including one or more executable instructions for implementing specified logical functions. It should be further noted that, in some alternative implementations, the functions denoted by the blocks may also occur in a sequence different from the sequences shown in the figures. For example, any two blocks presented in succession may be executed substantially in parallel, or they may sometimes be executed in a reverse sequence, depending on the functions involved. It should be further noted that each block in the block diagrams and/or flow charts as well as a combination of blocks in the block diagrams and/or flow charts may be implemented using a dedicated hardware-based system executing specified functions or operations, or by a combination of dedicated hardware and computer instructions.

The units involved in embodiments described in the present disclosure may be implemented by means of software or hardware. The described units may also be provided in a processor, for example, may be described as: a processor including an acquisition unit, a selection unit and a discrimination unit. Here, the names of these units do not in some cases constitute limitations to such units themselves. For example, the acquisition unit may also be described as "a unit configured to acquire a description text of the medical fact".

The above description only provides an explanation of embodiments of the present disclosure and the technical principles used. It should be appreciated by those skilled in the art that the inventive scope of the present disclosure is not limited to the technical solutions formed by the particular combinations of the above-described technical features. The inventive scope should also cover other technical solutions formed by any combinations of the above-described technical features or equivalent features thereof without departing from the concept of the present disclosure. Technical schemes formed by the above-described features being interchanged with, but not limited to, technical features with similar functions disclosed in the present disclosure are examples.

What is claimed is:

1. A method for verifying a medical fact, comprising:
acquiring a description text of the medical fact;
selecting a relevant paragraph related to the description text of the medical fact from a medical document;
selecting a target relevant paragraph having a highest relevance with the description text of the medical fact from the relevant paragraph using a trained discrimination model, the discrimination model being pre-trained based on a medical text paragraph pair extracted from the medical document, and being iteratively adjusted using a medical fact sample set including authenticity labeling information after the pre-training; and
determining that the medical fact is a correct description in response to determining that the relevance between the target relevant paragraph and the description text of the medical fact reaches a preset threshold.

2. The method according to claim 1, wherein the inputting the description text of the medical fact and the corresponding relevant paragraph into a trained discrimination model for authenticity judgment, to obtain a verification result of the medical fact, further comprises:
determining that the medical fact is a wrong description, in response to determining that the relevance between the relevant paragraph and the description text of the medical fact determined using the trained discrimination model does not reach the preset threshold.

3. The method according to claim 1, wherein the trained discrimination model is obtained by training as follows:
extracting two adjacent paragraphs from a same medical document as positive samples of the medical text paragraph pair, and extracting one paragraph from two different medical documents respectively as negative samples of the medical text paragraph pair;
pre-training a constructed initial discrimination model based on the positive samples and the negative samples of the medical text paragraph pairs;
acquiring the medical fact sample set including authenticity labeling information, wherein the authenticity labeling information comprises labeling information for labeling whether a medical fact sample is a correct description; and
adjusting iteratively the pre-trained discrimination model based on the medical fact sample set to obtain the trained discrimination model.

4. The method according to claim 3, wherein the authenticity labeling information further comprises a medical document paragraph that serves as supporting evidence for the medical fact sample when the medical fact sample is the correct description; and
the verification result of the medical fact comprises a verification result of whether the medical fact is the correct description and a medical document paragraph that serves as supporting evidence for the medical fact when the medical fact is the correct description.

5. An electronic device, comprising:
one or more processors; and
a storage configured to store one or more programs,
wherein the one or more programs, when executed by the one or more processors, cause the one or more processors to perform operations, the operations comprising:
acquiring a description text of a medical fact;
selecting a relevant paragraph related to the description text of the medical fact from a medical document;
selecting a target relevant paragraph having a highest relevance with the description text of the medical fact from the relevant paragraph using a trained discrimination model, the discrimination model being pre-trained based on a medical text paragraph pair extracted from the medical document, and being iteratively adjusted using a medical fact sample set including authenticity labeling information after the pre-training; and
determining that the medical fact is a correct description in response to determining that the relevance between the target relevant paragraph and the description text of the medical fact reaches a preset threshold.

6. The electronic device according to claim 5, wherein the inputting the description text of the medical fact and the corresponding relevant paragraph into a trained discrimination model for authenticity judgment, to obtain a verification result of the medical fact, further comprises:
determining that the medical fact is a wrong description, in response to determining that the relevance between the relevant paragraph and the description text of the medical fact determined using the trained discrimination model does not reach the preset threshold.

7. The electronic device according to claim 5, wherein the trained discrimination model is obtained by training as follows:
extracting two adjacent paragraphs from a same medical document as positive samples of the medical text paragraph pair, and extracting one paragraph from two different medical documents respectively as negative samples of the medical text paragraph pair;
pre-training a constructed initial discrimination model based on the positive samples and the negative samples of the medical text paragraph pairs;
acquiring the medical fact sample set including authenticity labeling information, wherein the authenticity labeling information comprises labeling information for labeling whether a medical fact sample is a correct description; and
adjusting iteratively the pre-trained discrimination model based on the medical fact sample set to obtain the trained discrimination model.

8. The electronic device according to claim 7, wherein the authenticity labeling information further comprises a medical document paragraph that serves as supporting evidence for the medical fact sample when the medical fact sample is the correct description; and
the verification result of the medical fact comprises a verification result of whether the medical fact is the correct description and a medical document paragraph that serves as supporting evidence for the medical fact when the medical fact is the correct description.

9. A non-transitory computer readable medium, storing a computer program thereon, wherein the program, when executed by a processor, causes the processor to perform operations, the operations comprising:
   acquiring a description text of a medical fact;
   selecting a relevant paragraph related to the description text of the medical fact from a medical document;
   selecting a target relevant paragraph having a highest relevance with the description text of the medical fact from the relevant paragraph using a trained discrimination model, the discrimination model being pre-trained based on a medical text paragraph pair extracted from the medical document, and being iteratively adjusted using a medical fact sample set including authenticity labeling information after the pre-training; and
   determining that the medical fact is a correct description in response to determining that the relevance between the target relevant paragraph and the description text of the medical fact reaches a preset threshold.

10. The non-transitory computer readable medium according to claim 9, wherein the inputting the description text of the medical fact and the corresponding relevant paragraph into a trained discrimination model for authenticity judgment, to obtain a verification result of the medical fact, further comprises:
   determining that the medical fact is a wrong description, in response to determining that the relevance between the relevant paragraph and the description text of the medical fact determined using the trained discrimination model does not reach the preset threshold.

11. The non-transitory computer readable medium according to claim 9, wherein the trained discrimination model is obtained by training as follows:
   extracting two adjacent paragraphs from a same medical document as positive samples of the medical text paragraph pair, and extracting one paragraph from two different medical documents respectively as negative samples of the medical text paragraph pair;
   pre-training a constructed initial discrimination model based on the positive samples and the negative samples of the medical text paragraph pairs;
   acquiring the medical fact sample set including authenticity labeling information, wherein the authenticity labeling information comprises labeling information for labeling whether a medical fact sample is a correct description; and
   adjusting iteratively the pre-trained discrimination model based on the medical fact sample set to obtain the trained discrimination model.

12. The non-transitory computer readable medium according to claim 11, wherein the authenticity labeling information further comprises a medical document paragraph that serves as supporting evidence for the medical fact sample when the medical fact sample is the correct description; and
   the verification result of the medical fact comprises a verification result of whether the medical fact is the correct description and a medical document paragraph that serves as supporting evidence for the medical fact when the medical fact is the correct description.

* * * * *